(12) United States Patent
Bae et al.

(10) Patent No.: US 10,991,559 B2
(45) Date of Patent: Apr. 27, 2021

(54) METHOD FOR QUANTITATIVE ANALYSIS OF POLYMER USING MALDI MASS SPECTROMETRY, AND METHOD FOR MANUFACTURING SAMPLE FOR MALDI MASS SPECTROMETRY FOR QUANTITATIVE ANALYSIS OF POLYMER

(71) Applicant: LG Chem, Ltd., Seoul (KR)

(72) Inventors: Yongjin Bae, Daejeon (KR); Jong Chan Kim, Daejeon (KR); Yeu Young Youn, Daejeon (KR); Young Hee Lim, Daejeon (KR); Hye Sung Cho, Daejeon (KR)

(73) Assignee: LG Chem, Ltd.

( * ) Notice: Subject to any disclaimer, the term of this patent is extended or adjusted under 35 U.S.C. 154(b) by 0 days.

(21) Appl. No.: 16/624,383

(22) PCT Filed: Sep. 11, 2018

(86) PCT No.: PCT/KR2018/010591
§ 371 (c)(1),
(2) Date: Dec. 19, 2019

(87) PCT Pub. No.: WO2019/074212
PCT Pub. Date: Apr. 18, 2019

(65) Prior Publication Data
US 2020/0219709 A1    Jul. 9, 2020

(30) Foreign Application Priority Data
Oct. 11, 2017    (KR) .................. 10-2017-0130010

(51) Int. Cl.
*H01J 49/04*    (2006.01)
*H01J 49/00*    (2006.01)
(Continued)

(52) U.S. Cl.
CPC ...... *H01J 49/0418* (2013.01); *H01J 49/0031* (2013.01); *H01J 49/0404* (2013.01); *H01J 49/164* (2013.01); *H01J 49/40* (2013.01)

(58) Field of Classification Search
CPC .............. H01J 49/0418; H01J 49/0031; H01J 49/0404; H01J 49/164; H01J 49/40
See application file for complete search history.

(56) References Cited

U.S. PATENT DOCUMENTS 7,858,387 B2    12/2010    DiCesare
2003/0138823 A1    7/2003    Brock et al.
(Continued)

FOREIGN PATENT DOCUMENTS

CN    102519779 B    6/2013
EP    1358012 B1    8/2008
(Continued)

OTHER PUBLICATIONS

International Search Report from PCT/KR2018/010591 dated Dec. 24, 2018, 2 pages.
(Continued)

*Primary Examiner* — Nicole M Ippolito
*Assistant Examiner* — Hanway Chang
(74) *Attorney, Agent, or Firm* — Lerner, David, Littenberg, Krumholz & Mentlik, LLP (57) ABSTRACT

The present invention provides a method enabling a quantitative analysis of a polymer by MALDI mass spectrometry, and a method for manufacturing a sample for MALDI mass spectrometry for a quantitative analysis of a polymer. To that end, the methods can increase reproducibility of a MALDI spectrum by making uniform the thickness of a sample affecting the pattern in a polymer MALDI spectrum. The sample according to the present invention is applicable also to a commercial MALDI-TOF instrument, and, thus, can
(Continued)

quantitatively analyze a polymer in a more efficient and faster manner.

12 Claims, 9 Drawing Sheets

(51) Int. Cl.
*H01J 49/16* (2006.01)
*H01J 49/40* (2006.01)

(56) References Cited

U.S. PATENT DOCUMENTS

| | | |
|---|---|---|
| 2004/0217276 A1 | 11/2004 | DiCesare |
| 2006/0138319 A1 | 6/2006 | Barnes et al. |
| 2008/0121796 A1 | 5/2008 | Green et al. |
| 2009/0197295 A1 | 8/2009 | Fournier et al. |
| 2016/0167065 A1 | 6/2016 | Takahashi |

FOREIGN PATENT DOCUMENTS

| | | |
|---|---|---|
| JP | 2006525525 A | 11/2006 |
| JP | 2007309860 A | 11/2007 |
| JP | 2011174887 A | 9/2011 |
| JP | 2012230801 A | 11/2012 |
| JP | 2014071075 A | 4/2014 |
| JP | 2014206389 A | 10/2014 |
| JP | 2016114400 A | 6/2016 |
| JP | 2016194513 A | 11/2016 |
| KR | 20050092809 A | 9/2005 |
| KR | 101434092 B1 | 8/2014 |
| KR | 20170013073 A | 2/2017 |
| KR | 20170021398 A | 2/2017 |
| WO | 2016041531 A1 | 3/2016 |

OTHER PUBLICATIONS

WIPS Intellectual Property Rights Search Report for KR20170130010 dated Jun. 8, 2017, 1 page.
WIPS Intellectual Property Rights Search Report for KR20170130010 dated May 2, 2018, 2 pages.

1) BHB-PPG + PPG sample

2) AP-PDMS + H-PDMS sample

BHB-PPG          PPG

AP(Allylphenol)-PDMS     H-PDMS

< Electrospray using a mask >   <Photomicrograph of specimen>

[Fig. 6]

Dried droplet   Electro spray

[Fig. 7]

1. Spot-to-spot evaluation of reproducibility

<BHB-PPG/PPG area ratio and error between spectra obtained from one specimen>

[Fig. 8]

2. Sample-to-sample evaluation of reproducibility

<BHB-PPG/PPG area ratio and error between spectra obtained from three specimens>

METHOD FOR QUANTITATIVE ANALYSIS OF POLYMER USING MALDI MASS SPECTROMETRY, AND METHOD FOR MANUFACTURING SAMPLE FOR MALDI MASS SPECTROMETRY FOR QUANTITATIVE ANALYSIS OF POLYMER

CROSS-REFERENCE TO RELATED APPLICATIONS

The present application is a national phase entry under 35 U.S.C. § 371 of International Application No. PCT/KR2018/010591, filed Sep. 11, 2018, which claims priority from Korean Patent Application No. 10-2017-0130010, filed Oct. 11, 2017, the disclosures of which are incorporated herein by reference.

BACKGROUND OF THE INVENTION

1. Field of the Invention

The present invention relates to a method for quantitative analysis of a polymer by MALDI mass spectrometry and a method for preparing a specimen for MALDI mass spectrometry for quantitative analysis of a polymer. More particularly, the present invention provides a method for quantitative analysis of a polymer and a method for preparing a specimen for MALDI mass spectrometry for quantitative analysis of a polymer, which enable to obtain a reproducible MALDI spectrum by using commercially available MALDI-TOF MS equipment.

2. Description of the Related Art

In order to obtain quantitative information through the mass spectrum, the reproducibility of the spectrum must be ensured under the same specimen and experimental conditions.

MALDI (Matrix-Assisted Laser Desorption Ionization) is known to be difficult to use for quantitative analysis because it lacks reproducibility of spectrum.

Recently, it has been reported that a reproducible MALDI spectrum can be obtained by constantly maintaining temperature of the MALDI plume for peptides and biomolecular materials. However, it has not been reported whether this technique is applicable to MALDI spectrometry for polymer. In addition, since such technique is not applicable to commercialized MALDI-TOF MS equipment, there is a disadvantage that it is difficult to utilize the technique.

SUMMARY OF THE INVENTION

The object of the present invention is to provide a method for quantitative analysis of a polymer using MALDI mass spectrometry by achieving a reproducible MALDI spectrum.

Another object of the present invention is to provide a method for preparing a specimen of a polymer sample suitable for obtaining a reproducible MALDI spectrum for the polymer.

In order to accomplish the object of the present invention, the present invention provides a method for quantitative analysis of a polymer using MALDI mass spectrometry with a specimen prepared by electrospray of a polymer sample, which is a mixed solution of a polymer compound, a matrix and a solvent, from a main nozzle onto a sample plate through a mask, wherein a thickness deviation in the specimen is 30% or less, and the mask comprises a hole through which the polymer sample to be electrosprayed can be passed to the sample plate.

According to one embodiment, in the specimen prepared under the above conditions, the error range of measurement results of the MALDI spectrum on the same specimen (a relative standard deviation (RSD) of results of three experiments) may be within 30%.

According to one embodiment, the error range of measurement results of the MALDI spectrum on at least three specimens prepared under the same condition may be within 30%.

According to one embodiment, the method for quantitative analysis may be for measuring a polymer having a molecular weight of 1000 Da or more.

In order to accomplish the other object of the present invention, there is provided by the method for preparing a specimen for MALDI mass spectrometry for quantitative analysis of a polymer, using the electrospray apparatus according to the present invention comprising a main nozzle for electrospray of a polymer sample which is a mixed solution of a polymer compound, a matrix and a solvent, and a sample plate on which the specimen is placed by electrospray of the polymer sample, the method comprising the steps of:

mounting a mask on the sample plate;

performing electrospray of the polymer sample from the main nozzle onto the sample plate provided with the mask; and obtaining the specimen of the polymer compound on the sample plate, wherein the mask may comprise a hole through which the polymer sample to be electrosprayed from the main nozzle, can be passed to the sample plate so as to obtain a uniform specimen having a small thickness deviation on the sample plate.

In addition, in the method for preparing a specimen for MALDI mass spectrometry for quantitative analysis of a polymer according to the present invention, the diameter of the hole may be 1 µm to 2 µm.

In addition, in the method for preparing a specimen for MALDI mass spectrometry for quantitative analysis of a polymer according to the present invention, the material of the mask is not particularly limited, and for example, stainless steel, aluminum, or the like can be used.

In addition, in the method for preparing a specimen for MALDI mass spectrometry for quantitative analysis of a polymer according to the present invention, the step of mounting the mask on the sample plate may further comprise adjusting the position of the mask in at least one of x-axis, y-axis, and z-axis directions.

In addition, in the method for preparing a specimen for MALDI mass spectrometry for quantitative analysis of a polymer according to the present invention, the electrospray apparatus further comprises an auxiliary nozzle surrounding the main nozzle and coaxial with the main nozzle, and the step of performing electrospray of the polymer sample from the main nozzle onto the sample plate may further comprise spraying the solvent from the auxiliary nozzle to prevent the matrix from being deposited in the vicinity of the main nozzle.

In addition, in the method for preparing a specimen for MALDI mass spectrometry for quantitative analysis of a polymer according to the present invention, the electrospray apparatus further comprises a sheath gas supply pipe surrounding the auxiliary nozzle and coaxial with the auxiliary nozzle, and the step of performing electrospray of the polymer sample from the main nozzle onto the sample plate may further comprise jetting a sheath gas through the sheath gas supply pipe so that the sheath gas guides the polymer sample to be sprayed onto the predetermined position of the sample plate.

In addition, in the method for preparing a specimen for MALDI mass spectrometry for quantitative analysis of a polymer according to the present invention, using an electrospray apparatus comprising a main nozzle for electrospray of a polymer sample which is a mixed solution of a polymer compound, a matrix and a solvent, and a sample plate on which the specimen is placed by electrospray of the polymer sample, the method comprises the steps of:

performing electrospray of the polymer sample from the main nozzle onto the sample plate; and obtaining a specimen of the polymer sample on the sample plate, wherein the step of performing electrospray of the polymer sample from the main nozzle onto the sample plate further comprises at least one steps of (i) spraying the solvent from an auxiliary nozzle surrounding the main nozzle and coaxial with the main nozzle, so as to prevent the matrix from being deposited in the vicinity of the main nozzle, and (ii) jetting a sheath gas through a sheath gas supply pipe so that the sheath gas guides the polymer sample to be sprayed onto the predetermined position of the sample plate, so as to obtain a uniform specimen having a small thickness deviation on the sample plate.

In addition, in the method for preparing a specimen for MALDI mass spectrometry for quantitative analysis of a polymer according to the present invention, the jetting area through electrospray is 80 mm$^2$ or less.

Effect of the Invention

The present invention provides a method for quantitative analysis of a polymer by MALDI mass spectrometry and a method for preparing a specimen for MALDI mass spectrometry for quantitative analysis of a polymer, in which the reproducibility of the MALDI spectrum can be further improved by uniformizing the thickness of the specimen that affects the pattern in the MALDI spectrum of polymer. Since the specimen according to the present invention is applicable to commercial MALDI-TOF equipment, quantitative analysis of the polymer can be performed more efficiently and quickly.

DETAILED DESCRIPTION OF THE INVENTION

Since various modifications and variations can be made in the present invention, particular embodiments are illustrated in the drawings and will be described in detail in the detailed description. It should be understood, however, that the invention is not intended to be limited to the particular embodiments, but includes all modifications, equivalents, and alternatives falling within the spirit and scope of the invention. In the following description of the present invention, detailed description of known functions will be omitted if it is determined that it may obscure the gist of the present invention.

In addition, the same or corresponding components will be denoted by the same reference numerals regardless of symbols, and redundant description thereof will be omitted. For convenience of explanation, the size and shape of each component shown may be exaggerated or reduced.

Hereinafter, the present invention will be described in more detail.

The present invention provides a method for quantitative analysis of a polymer using MALDI mass spectrometry with a specimen prepared by electrospray of a polymer sample, which is a mixed solution of a polymer compound, a matrix and a solvent, from a main nozzle onto a sample plate through a mask, wherein a thickness deviation in the specimen is 40% or less, or 30% or less, or 20% or less and the mask comprises a hole through which the polymer sample to be electrosprayed can be passed to the sample plate.

Figure 1:
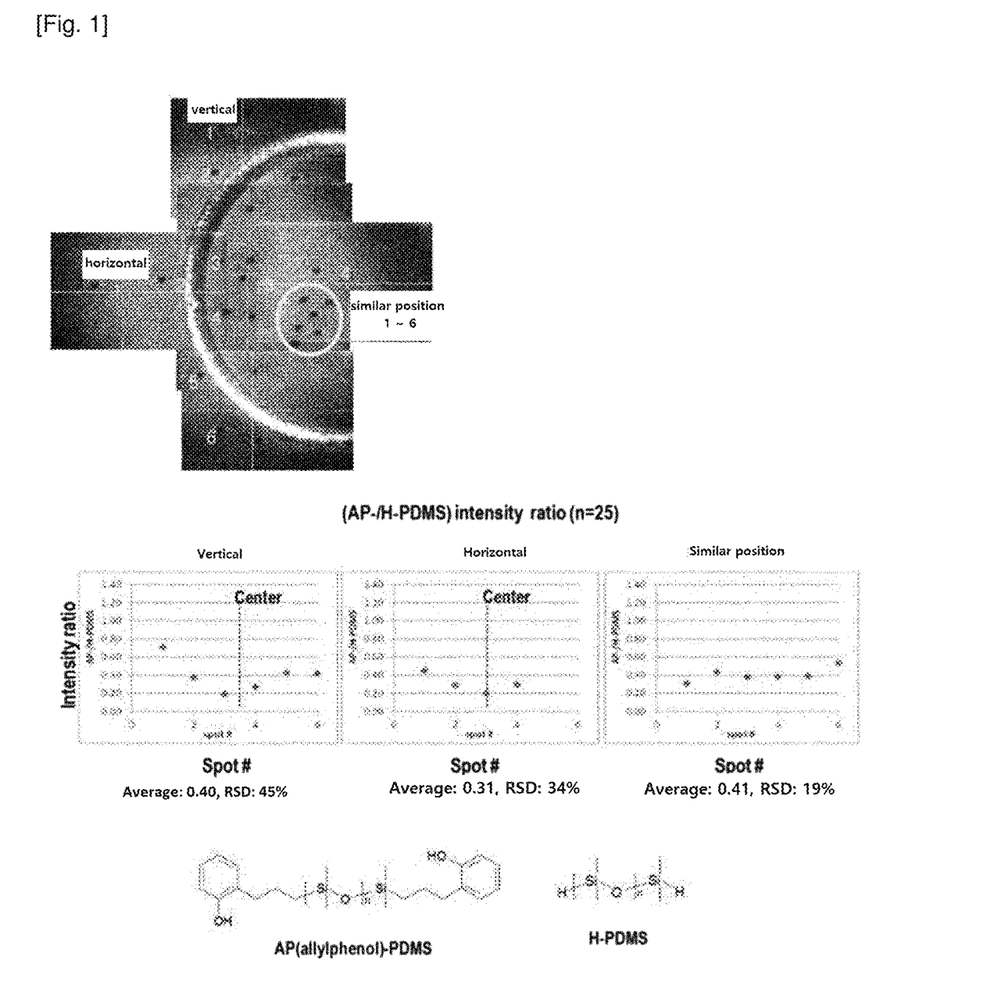
FIG. 1 shows the difference of MALDI spectrum according to the analysis spot in the specimen manufactured by a conventional technique.

From MALDI spectra obtained at various spots of polymer specimens prepared by conventional method, it was found that the spectrum for center of the specimen and the spectrum for edge of the specimen were different from each other. Referring to FIG. 1, it shows that the spectrum varies with remarkable tendency from the center toward the edge of the specimen and the spectra measured at similar spots exhibit a comparatively similar tendency. Generally, when the temperatures of the plumes are the same, the spectrum tends to match, which means that the tendency of the spectrum can be different when the temperatures of the plumes are different. Therefore, the results of FIG. 1 indicate that the temperatures of the plumes vary depending on the spots in the specimen. In addition, the temperatures of the plumes are related to the thickness of the specimen, and the temperatures of the plumes tend to increase as the thickness increases. From this general fact, it can be predicted that the thickness of the specimen is a factor affecting the pattern in the MALDI spectrum of polymer.

Figure 2:
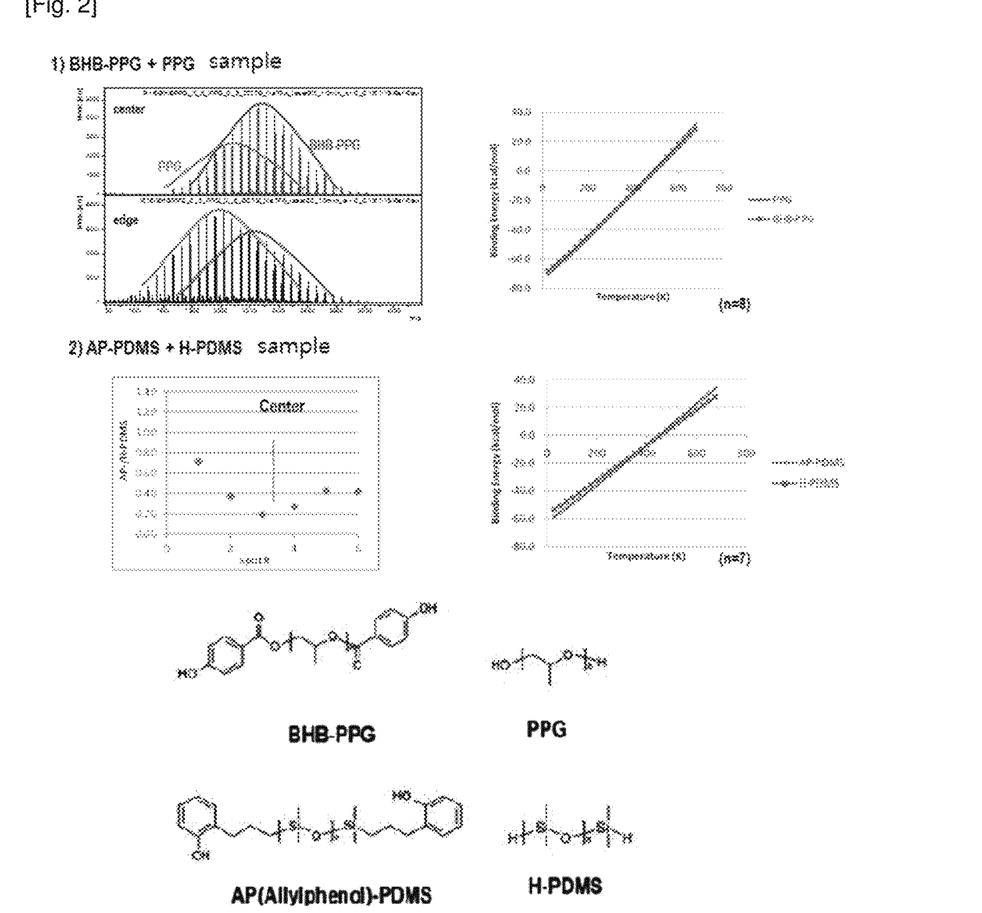
FIG. 2 shows the variation of the MALDI spectrum according to the thickness of the specimen and the difference of ionization efficiency according to the temperature of the MALDI plumes.

FIG. 2 shows the influence of the temperature change depending on the thickness of the specimen on the ionization efficiency of the polymer. Referring to the change of the spectrum intensity depending on the analysis spots in the specimen of the BHB-PPG+PPG sample (1) in FIG. 2, it can be seen that the signal intensity ratio of BHB-PPG to PPG is larger at the center than that at the edge of the specimen. The cause of the phenomenon can be predicted from the graph showing a change in binding energy of Na+ and polymer depending on the temperature. The graph on the right side of FIG. 2 is a graph of a change in binding energy of Na+ and polymer depending on the temperature. The binding energy of Na+ and polymer can be obtained from the following equation:

$$\text{Binding energy}=E(\text{Na}^+,\text{polymer})-(E(\text{Na}^+))+E(\text{polymer}))$$

In the above equation, E(Na+) and E(polymer) refers to the energy of Na+ and polymer, respectively, and E(Na+, polymer) refers to the energy of the structure in which Na+ and polymer are combined. The optimized structure and energy of a molecule can be determined from density functional theory (DFT). The lower the binding energy of Na+ and polymer is, the higher the affinity of Na+ is. Therefore, it can be predicted that as the temperature increases, BHB-PPG will have more ions generated relative to PPG. In the case of the AP-PDMS+H-PDMS sample (2) of FIG. 2, the experimental result can be predicted by using a graph of the change in binding energy of Na$^+$ and polymer depending on the temperature. From these results, it can be seen that the temperatures of the plumes can influence on the ionization efficiency. In general, such temperatures variation of plumes can result from differences in specimen thickness. Therefore, it is found that a specimen having a uniform thickness should be used in order to obtain a uniform and reproducible MALDI spectrum.

Therefore, in the present invention, by using a specimen having a thickness deviation of 40% or less, or 30% or less, or 20% or less, prepared by electrospray through a mask for measuring the MALDI spectrum of a polymer, a reproducible MALDI spectrum can be obtained, thereby enabling quantitative analysis of the polymer.

The MALDI spectrum of polymer according to the present invention may have 30% or less of RSD (Relative Standard Deviation) of results of three or more trials under same condition. For example, in the case of spot-to-spot evaluation for three or more points in the same specimen, an error may be within 30%, preferably within 20%, and more preferably within 15%. Reproducible MALDI spectra can be obtained with an error within 30% even in the case of sample-to-sample evaluation for three or more specimens prepared under same condition.

The present invention also provides a method for preparing a specimen of a polymer sample suitable for obtaining a reproducible MALDI spectrum of polymer as described above.

Therefore, in order to produce a specimen having uniform thickness as described above, there is provided by a method for preparing a specimen for MALDI mass spectrometry for quantitative analysis of a polymer, using an electrospray apparatus comprising a main nozzle for electrospray of a polymer sample which is a mixed solution of a polymer compound, a matrix and a solvent, and a sample plate on which the specimens are placed by electrospray of the polymer sample, the method comprising the steps of:

mounting a mask on the sample plate;

performing electrospray of the polymer sample from the main nozzle onto the sample plate provided with the mask; and obtaining the specimens of the polymer compound on the sample plate, wherein the mask may comprise a hole through which the polymer sample to be electrosprayed from the main nozzle, can be passed to the sample plate so as to obtain a uniform specimen having a small thickness deviation on the sample plate.

In order to obtain a reproducible MALDI spectrum, it is most important to fabricate specimens with a small thickness deviation by controlling the thickness of the specimen. For this purpose, in the present invention, the MALDI spectrum was measured by selecting only the center of the jetting region with the sample using electrospray through a mask. In this way, a uniform specimen with a small thickness deviation can be produced. The polymer specimen prepared by this method can be applied to a commercial MALDI-TOF MS equipment and provide a reproducible MALDI spectrum with error range within 30%. From this, it is possible to quantitatively analyze a polymer sample.

According to the method using electrospray, the polymer sample can be sprayed and deposited more uniformly over a large area. Electrospray has a simple shape and structure of nozzle so that it is easy to be manufactured and it makes simple to generate several tens of micro-sized to several hundreds of nano-sized droplets. In addition, since the droplets have a monodisperse distribution and the surface of the droplet is charged, there is an advantage that the droplets are hardly to be bonded to each other and it is easy to control the droplet. In addition, it is possible to manufacture a specimen which has a large area, can be prepared by jetting at atmospheric pressure and has more stable characteristics due to electrostatic effect.

Figure 3:
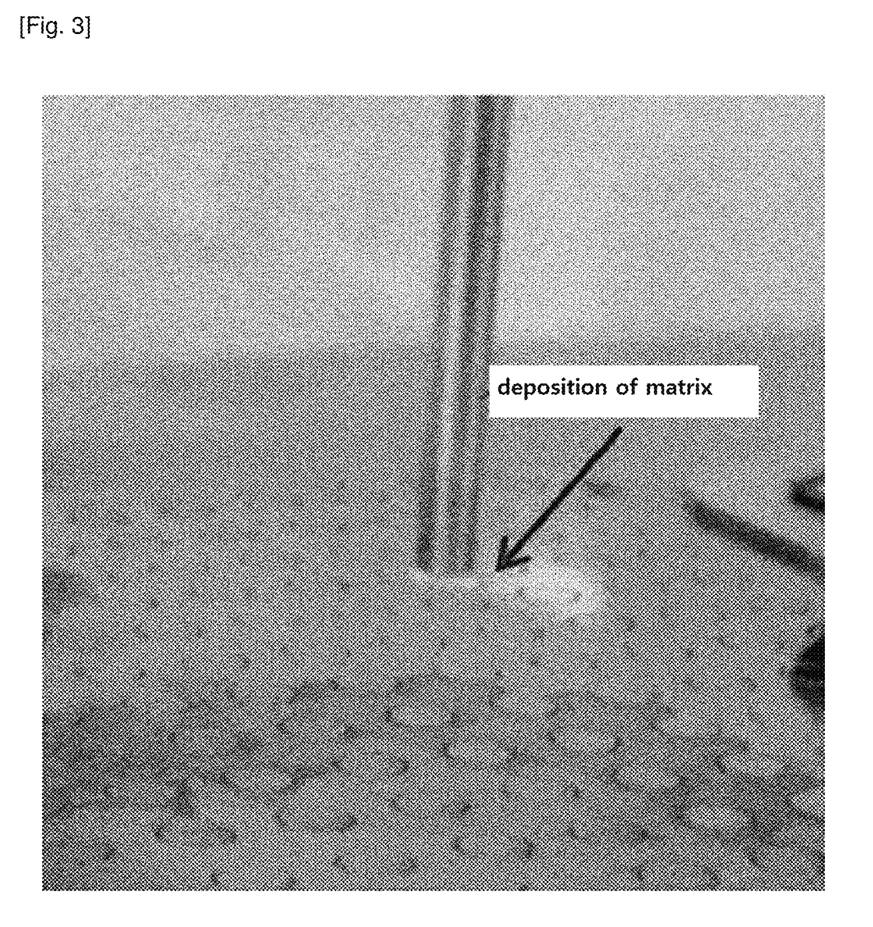
FIG. 3 shows a phenomenon in which a matrix is deposited at the end of a nozzle in jetting process using a conventional electrospray.

On the other hand, in the jetting process using the electrospray according to the related art, when a mixed solution of a polymer compound, a matrix and a solvent is sprayed, there is a phenomenon of deposition of the matrix at the end of the nozzle and thus there is a problem that reproducibility of electrospray of the sample is deteriorated due to the deposited matrix at the end of the nozzle (see FIG. 3). That is, it is difficult for the sample to be jetted to a predetermined position due to the matrix deposited at the end of the nozzle.

Figure 4A:
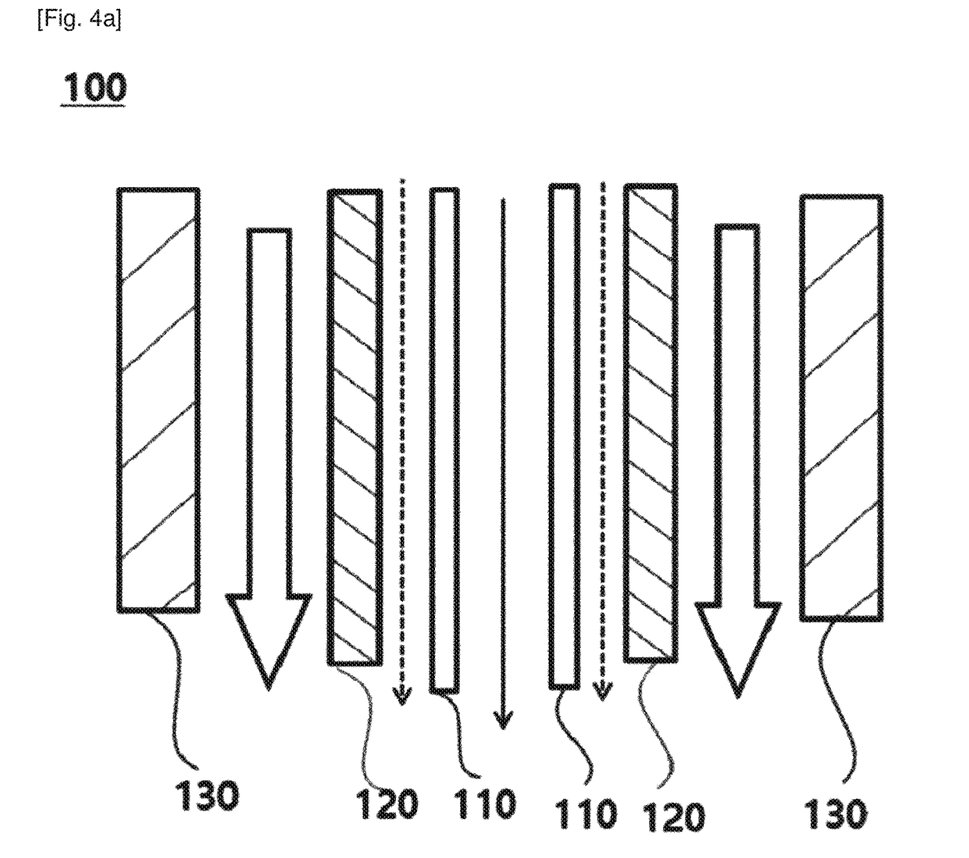
FIG. 4a to 4e show an apparatus for manufacturing a specimen through electrospray according to an embodiment of the present invention.

In the jetting process using electrospray in the method of preparing a specimen through electrospray according to an embodiment of the present invention, a nozzle unit 100 of an electrospray apparatus 10 (see FIG. 4e) comprises a main nozzle 110 through which a mixed solution (hereinafter referred to as a "polymer sample" or a "sample") of a polymer compound, a matrix and a solvent, and an auxiliary nozzle 120 surrounding the main nozzle 110 and coaxial with the main nozzle 110 and the auxiliary nozzle 120 is configured to spray the solvent, as shown in FIG. 4a relating to a cross-sectional view of a nozzle used in the method of preparing a specimen through electrospray according to an embodiment of the present invention. In FIG. 4a, solid arrows in the main nozzle 110 indicate a flow of the polymer sample jetted from the main nozzle 110, and arrows indicated by dotted lines in the auxiliary nozzle 120 indicate a flow of the polymer sample jetted from the auxiliary nozzle 120. That is, by jetting the solvent from the auxiliary nozzle 120 surrounding the main nozzle 110 while jetting the polymer sample from the main nozzle 110, it is possible to prevent deposition of the matrix at the end of the nozzle, which is a problem in the jetting process using electrospray according to the prior art, thereby improving the reproducibility of electrospray of the polymer sample. That is, the polymer sample to be electrosprayed from the main nozzle 110 can be sprayed to a predetermined position. The inlet of the main nozzle 110 may protrude further toward the sample plate relative to the inlet of the auxiliary nozzle 120. For example, the inlet of the main nozzle 110 may protrude further toward the sample plate relative to the inlet of the auxiliary nozzle 120 by about 1 mm to 2 mm. The amount of solvent jetted from the auxiliary nozzle 120 may be, for example, 30 to 60% of the amount of solvent jetted from the main nozzle 110.

Additionally or alternatively, with a sheath gas supply pipe 130 surrounding the auxiliary nozzle 120 and coaxial with the auxiliary nozzle 120, when a polymer sample is sprayed through the main nozzle 110, the sheath gas is also sprayed around the polymer sample so that the sheath gas guides the polymer sample to be sprayed onto the predetermined position. In FIG. 4a, a thick arrow in the sheath gas supply pipe 130 indicates a sheath gas jetted from the sheath gas supply pipe 130. Accordingly, the reproducibility of electrospray of the polymer sample can be improved. As the sheath gas, for example, nitrogen gas ($N_2$) may be used. For example, the nitrogen gas can be released at 100 cc to 1000 cc per minute, and in one embodiment, 1000 cc per minute.

Figure 4B:
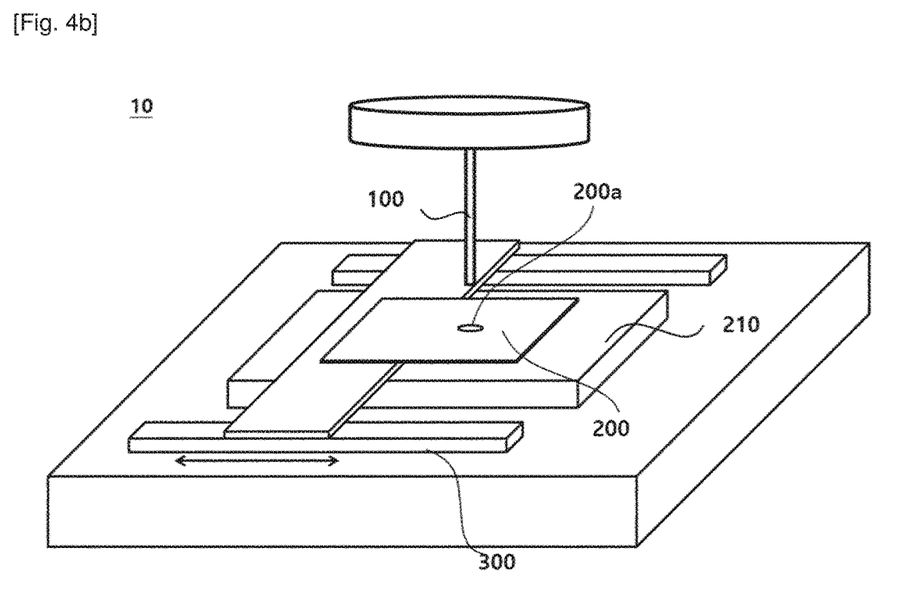

In summary, according to the present invention, while jetting a polymer sample, which is a mixed solution of a polymer compound, a matrix and a solvent, through a main nozzle 110, the solvent is jetted through an auxiliary nozzle 120 surrounding the main nozzle 110 or a sheath gas is jetted through a sheath gas supply pipe surrounding the auxiliary nozzle 120 and coaxial with the auxiliary nozzle 120 around the polymer sample to be jetted. Thereby, the polymer sample to be electrosprayed from the main nozzle 110 can be sprayed to a predetermined position on the sample plate. In addition, in the method of preparing a specimen via electrospray according to an embodiment of the present invention, as shown in FIG. 4b, when preparing a specimen of a polymer compound, a mask 200 according to an embodiment of the present invention, and a unit for adjusting mask position 300 may be used. That is, when the polymer sample is electrosprayed onto the sample plate placed on the sample stage 210, a mask 200 that can be positioned on the sample plate is used. Thereby, the polymer sample can be selected so that only a portion with small thickness deviation can be selected as a specimen, among the regions to be spread widely on the sample plate placed on the sample stage 210 due to electrospray. In addition, the mask 200 may be mounted on the unit for adjusting mask position 300 and positioned on the sample plate, and the position of the mask 200 may be adjusted by the unit for adjusting mask position 300.

At the center of the mask 200, there is a hole 200a having a size of substantially identical with a size of a specimen corresponding to a portion having a desired thickness deviation. The sample which cannot pass through the hole 200a among the samples to be electrosprayed remains on the mask 200. With the improved reproducibility of electrospray of the polymer sample as described above with reference to FIG. 4a, if the mask 200 according to FIG. 4b is mounted on the sample plate, the polymer sample to be electrosprayed may be placed on the sample plate through the hole 200a of the mask 200 to obtain a specimen having a desired thickness deviation. As a result, finally a specimen having a desired thickness deviation remains on the sample stage 210. The material of the mask 200 is not particularly limited, and for example, stainless steel, aluminum, or the like can be used.

The shape of the mask 200 may be, for example, a rectangular shape, a circular shape or the like, but the present invention is not limited thereto, and various modifications and variations are possible. When the mask 200 has, for example, a rectangular shape, the length of one side may be, for example, 1 mm to 2 mm, and when the mask 200 has, for example, a circular shape, the diameter may be 1 mm to 2 mm. The size of the hole 200a may be, for example, 1 μm to 2 μm in diameter.

Figure 4C:
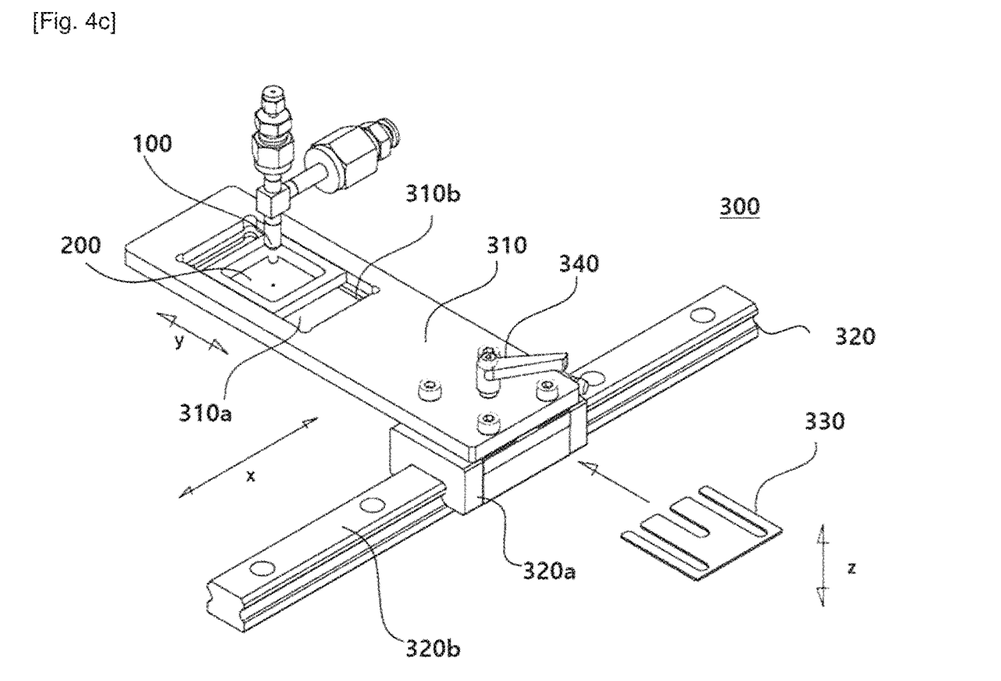

Next, referring to FIG. 4c, the unit for adjusting mask position 300 comprises a mask holder 310 on which the mask 200 can be mounted.

The mask holder 310 may further comprise, in an embodiment, an opening 310a. The mask 200 may be mounted on the opening 310a and the mounted mask 200 may move on an axis in one direction (e.g., the y-axis). The opening 310a may have, for example, a rectangular shape, and the width of one side of the rectangular shape of opening 310a may coincide with the width of the mask 200. The width of the other side of the opening 310a is larger than the width of the mask 200 so that the mask 200 mounted on the opening 310a can be moved and mounted. A convex portion 310b is provided at both edges of the opening 310a. Accordingly, the mask 200 can be placed over the convex portion 310b of the opening 310a.

The unit for adjusting mask position 300 comprises a linear motion rail 320 extending perpendicularly to the longitudinal direction of a mask holder 310. The mask holder 310 may be mounted on a mounting portion 320a of the linear motion rail 320. The mask holder 310 is fixed to the mounting portion 320a with bolts or the like so that it can move in the x-axis on a rail portion 320b of the linear motion rail 320. The rail portion 320b may further comprise a ruler (see FIG. 4d) to indicate how much the mask holder 310, that is, the mask 200 mounted on the mask holder 310, moves in the x-axis.

If the mask holder 310 moves in the x-axis on the linear motion rail 320, the mask 200 may move in the y-axis direction within the opening 310a of the mask holder 310 as described above. In addition, the unit for adjusting mask position 300 can adjust the height of the mask holder 310 in the z-axis direction (perpendicular to the upper surface of the sample stage 210). As the plate on which the specimen is placed, for example, a plate of stainless steel, an ITO glass, or the like is variously used. Therefore, it is necessary to adjust the mask holder 310, that is, the height (height in the z-axis direction) of the mask 200 mounted on the mask holder 310, to match the height of the plate. When the mask holder 310 is mounted on the mounting portion 320a of the linear motion rail 320, a spacer 330 may be provided between the mask holder 310 and the mounting portion 320a to adjust the height of the mask holder 310. For example, while increasing the number of spacers from 0 (zero), a plurality of spacers may be provided until the corresponding height is reached, or a spacer having a height corresponding to the plate may be provided. The present invention is not limited to the embodiments described above, and various modifications and variations thereof are possible.

The unit for adjusting mask position 300 according to the present invention may further comprise a fixing portion 340 for fixing the mask holder 310 on the linear motion rail 320.

Figure 4D:
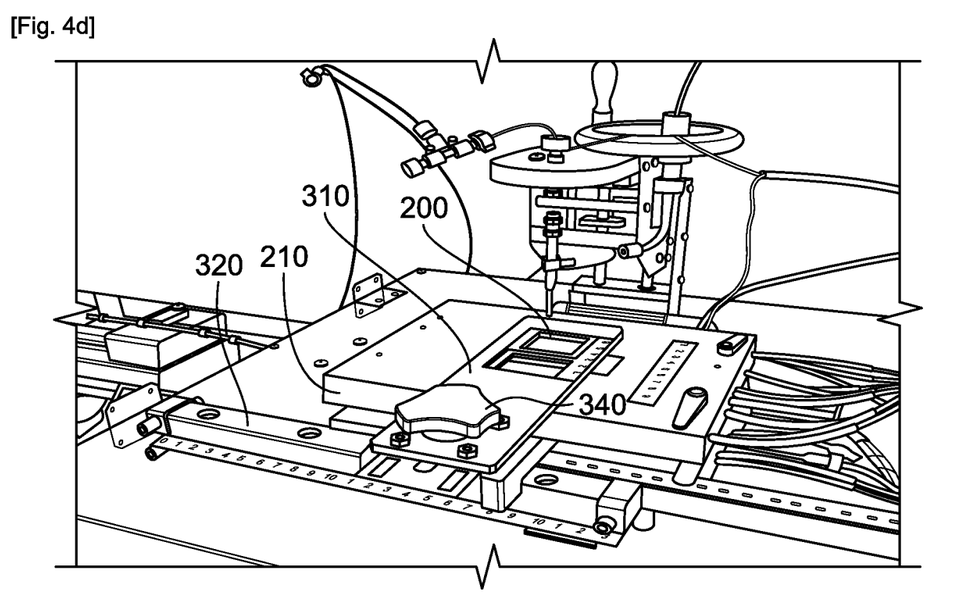

FIG. 4d shows a photograph of the mask 200 and the unit for adjusting mask position 300 of FIG. 4b and FIG. 4c which are implemented in one embodiment.

In summary, in the method of preparing a specimen by electrospray according to an embodiment of the present invention, the mask 200 according to FIGS. 4b to 4d is placed on the sample plate so that only a portion with small thickness deviation can be selected as a specimen, among the regions to be spread widely when electrospraying the polymer sample on the sample plate on the sample stage 210, while in order to adjust the position of the mask 200, the movement in the z-axis direction of the mask holder 310 on which the mask 200 is mounted is controlled by the spacers 330 between the mask holder 310 and the linear motion rail 320, the movement in the x-axis direction of the mask holder 310 on which the mask 200 is mounted is controlled by the linear motion rail 320 and the movement in the y-axis direction of the mask 200, and the mask 200 can be moved in the y-axis direction within the opening 310a of the mask holder 310. The method of adjusting the position of the mask described above is an embodiment of a method of preparing a specimen using the mask of the present invention. The present invention is not limited to the above-described method, and various modifications and variations thereof are possible regarding the manner of adjusting the position of the mask.

Figure 4E:
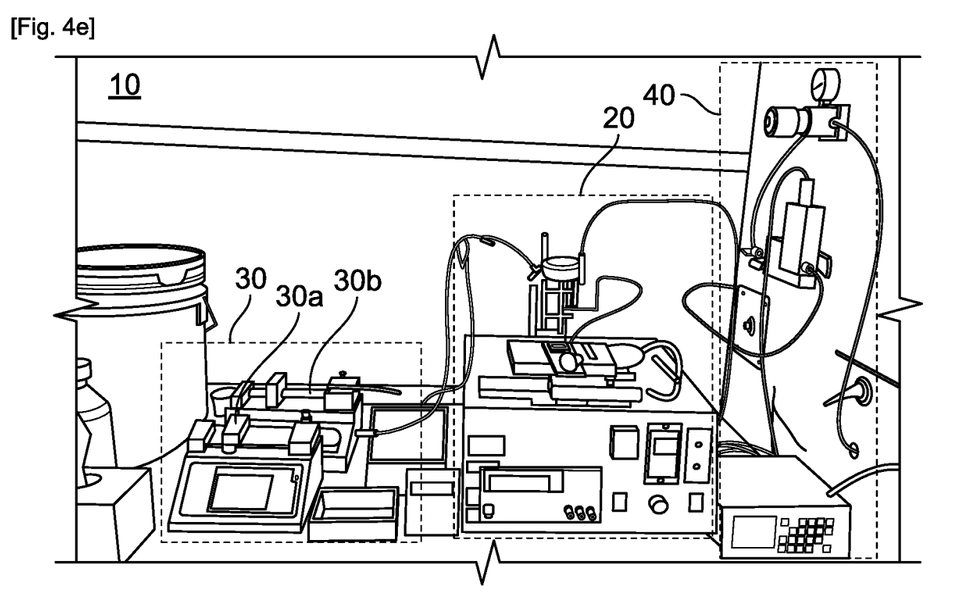

FIG. 4e shows a photograph of an embodiment of the electrospray apparatus 10 for producing a specimen according to the present invention. The main body 20 comprises the nozzle unit 100 including the main nozzle 110, the auxiliary nozzle 120 and the sheath gas supply pipe 130 of FIG. 4a, and the mask 200, the sample stage 210 and the unit for adjusting mask position 300 of FIGS. 4b and 4c. A unit for adjusting injection amount of sample 30 may comprise a pump 30a for controlling the injection amount of the polymer sample supplied to the main nozzle 110 of FIG. 4a and a pump 30b for controlling the injection amount of the solvent supplied to the auxiliary nozzle 120. A unit for adjusting sheath gas 40 can regulate the amount of sheath gas supplied to the sheath gas supply pipe 130 of FIG. 4a.

According to one embodiment, the jetting area through electrospray may be 80 mm$^2$ or less.

According to one embodiment, the polymer that can be applied to MALDI mass spectrometry according to the present invention is not particularly limited as long as it is a polymer having a molecular weight of 1000 Da or more.

Hereinafter, embodiments of the present invention will be described in detail so that those skilled in the art can easily carry out the present invention. The present invention may, however, be embodied in many different forms and should not be construed as limited to the embodiments set forth herein.

Preparation Example 1

A solution of the polymer compound of BHB-PPG/PPG dissolved in tetrahydrofuran (THF) was mixed with a solution (10 mg/ml) of a matrix (DCTB, trans-2-[3-(4-tert-butylphenyl)-2-methyl-2-propenylidene]malononitrile) and a NaTFA solution (0.02M in THF) at a volume ratio of 9:1:1 to prepare a polymer sample.

BHB-PPG

PPG

Comparative Example 1

By using the polymer sample prepared in Preparation Example 1, MALDI spectra were measured for six spots of each of two specimens prepared by the Dried droplet method (MALDI-TOF MS equipment: UltrafleXtreme, Bruker Daltonics, Germany).

Example 1

Figure 5:
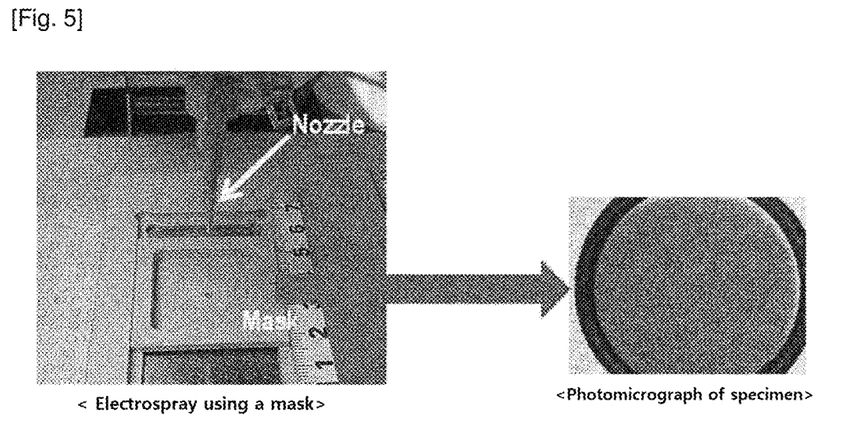
FIG. 5 shows a process for manufacturing a specimen for electrospray using the mask according to an embodiment of the present invention and a photomicrograph of the specimen manufactured according to an embodiment of the present invention.

By using the polymer sample prepared in Preparation Example 1 and the electrospray apparatus 10 as shown in FIG. 4e and the mask 200 as shown in FIG. 4d, MALDI spectra were measured for six spots of each of two specimens prepared as in FIG. 5.

Figure 6:
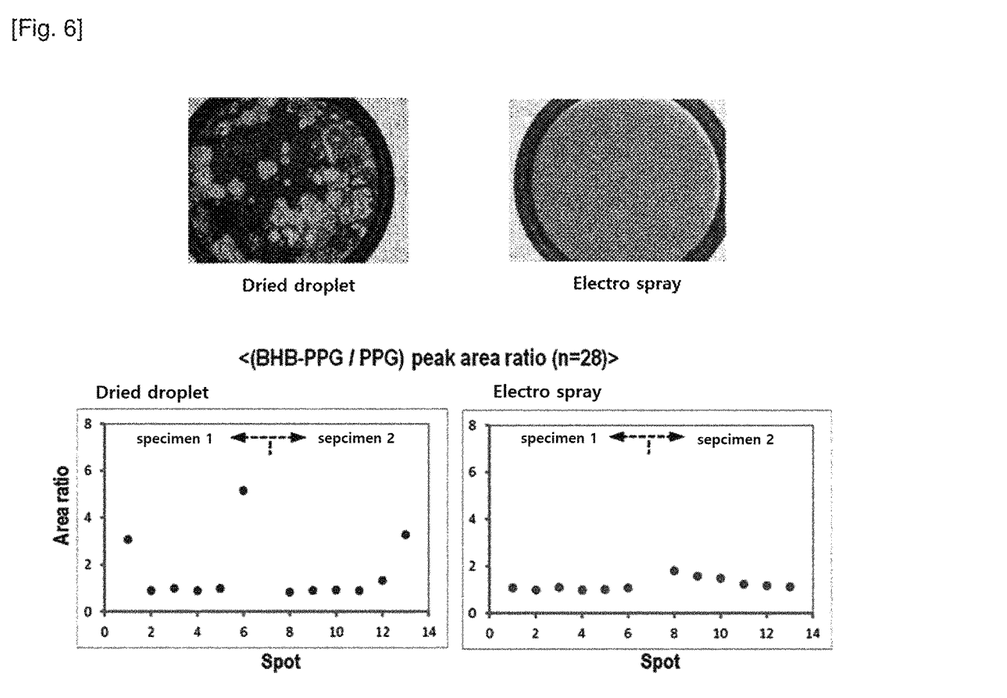
FIG. 6 shows the specimen prepared according to the Dried droplet method and the specimen prepared according to one embodiment of the present invention, and the reproducibility of the MALDI spectrum for the above specimens.

The MALDI-TOF spectra of the specimens prepared in Comparative Example 1 and Example 1 are shown in FIG. 6. As shown in FIG. 6, the reproducibility of spectrum is higher in the specimen of Example 1 manufactured using the electrospray and the mask.

Experimental Example 1. Spot-to-Spot Evaluation of Reproducibility

The specimens were prepared in the same manner as in Example 1, using the polymer samples having the BHB-PPG and PPG concentrations of 0.5 (mg/mL)/0.5 (mg/mL), 1.0 (mg/mL)/0.5 (mg/mL) and 3.0 (mg/mL)/0.5 (mg/mL), respectively.

To attain MALDI spectrum, a specimen is generally prepared by electrospray of a polymer sample on a stainless steel plate at a flow rate (1$^{st}$ flow) of 0.5 μL/min for 10 minutes. However, the stainless steel plate has a rough surface and thus it is not suitable for measuring thickness of specimen. Therefore, in the case of measuring the thickness of the electrosprayed specimen, the polymer sample is electrosprayed onto an ITO glass at a flow rate (1$^{st}$ flow) of 0.5 μL/min for 10 minutes, and then the thickness of the specimen was measured at 2 μm intervals using an optical profiler. The average thickness for the measured thickness profile was about 1 μm. Assuming that the spot size of the MALDI laser is 50 μm, the standard deviation of the average of the 25 measured values was measured and as a result, the thickness deviation was about 25%.

For each specimen, MALDI-TOF spectra were measured three times or more at three different points. The measurement results are shown in FIG. 7.

Figure 7:
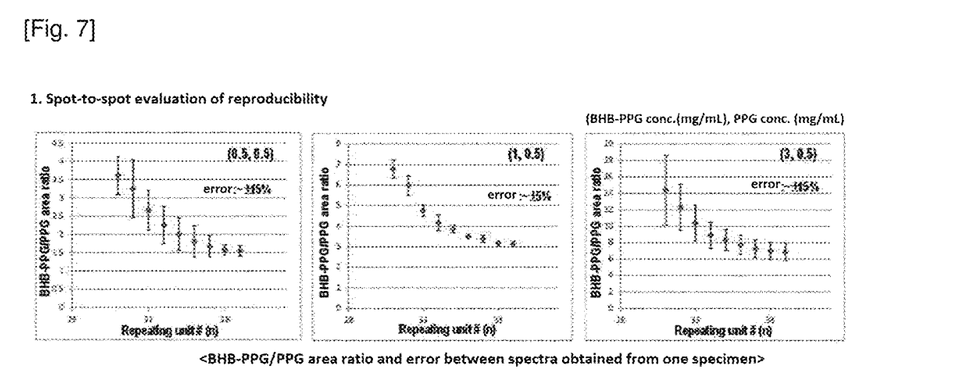
FIG. 7 shows results of spot-to-spot evaluation of reproducibility of MALDI-TOF spectra for specimens prepared according to one embodiment.

According to the results of FIG. 7, the specimens prepared by the method according to the present invention has an error range within 15% of the spectrum measured at different points in the same specimen, and an error range of at least 5%. Therefore, highly reproducible MALDI spectral results can be attained.

Experimental Example 2. Sample-to-Sample Evaluation of Reproducibility

Three specimens were prepared for each concentration in the same manner as in Example 1, using the polymer samples having BHB-PPG and PPG concentrations of 0.5 (mg/mL)/0.5 (mg/mL), 1.0 (mg/mL)/0.5 (mg/mL) and 3.0 (mg/mL)/0.5 (mg/mL), respectively.

To attain MALDI spectrum, a specimen is generally prepared by electrospray of a polymer sample on a stainless steel plate at a flow rate (1$^{st}$ flow) of 0.5 μL/min for 10 minutes. However, the stainless steel plate is a rough surface and thus it is not suitable for measuring thickness of specimen. Therefore, in the case of measuring the thickness of the electrosprayed specimen, the polymer sample is electrosprayed onto an ITO glass at a flow rate ($1^{st}$ flow) of 0.5 µL/min for 10 minutes, and then the thickness of the specimen was measured at 2 µm intervals using an optical profiler. The average thickness for the measured thickness profile was about 1 µm. Assuming that the spot size of the MALDI laser is 50 µm, the standard deviation of the average of the 25 measured values was measured and as a result, the thickness deviation was about 25%.

Figure 8:
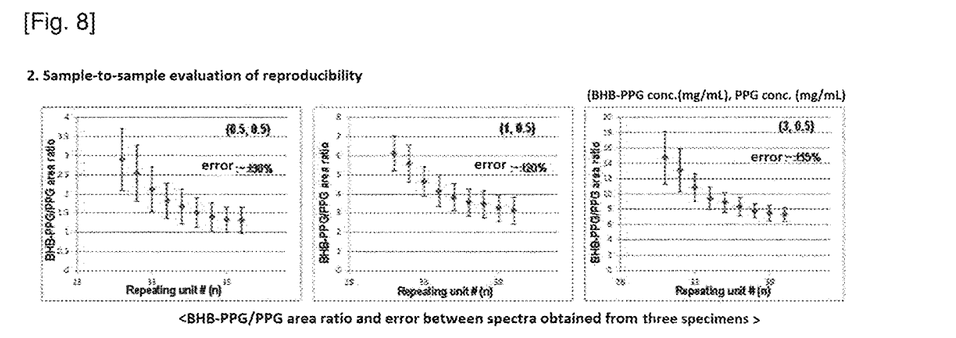
FIG. 8 shows results of sample-to-sample evaluation of reproducibility of MALDI-TOF spectra for three or more specimens prepared under the same condition according to one embodiment.

The reproducibility was evaluated by MALDI-TOF measurement on three specimens having the same concentration condition, respectively, and the result is shown in FIG. 8.

According to the results as shown in FIG. 8, the specimens prepared by the method according to the present invention exhibit an error range within 30% of the MALDI spectrum for the specimens prepared under the same condition. Therefore, if the specimens are manufactured under the same condition, a reproducible MALDI spectrum can be attained.

While the present invention has been particularly shown and described with reference to specific embodiments thereof, it will be apparent to those skilled in the art that this specific description is merely a preferred embodiment and that the scope of the invention is not limited thereby. It is therefore intended that the scope of the invention be defined by the claims appended hereto and their equivalents.

DESCRIPTION OF SYMBOLS

| | |
|---|---|
| 10: Electrospray apparatus | 100: Nozzle unit |
| 110: Main nozzle | 120: Auxiliary nozzle |
| 130: Sheath gas supply pipe | 200: Mask |
| 200a: Hole | 210: Sample stage |
| 300: Unit for adjusting mask position | |
| 310: Mask holder | |
| 310a: Opening | 310b: Convex portion |
| 320: Linear motion rail | 320a: Mounting portion |
| 320b: Rail portion | 330: Spacer |
| 340: Fixing portion | 20: Main body |
| 30: Unit for adjusting injection amount of sample | |
| 40: Unit for adjusting sheath gas | |

What is claimed is:

1. A method for quantitative analysis of a polymer using MALDI mass spectrometry, comprising:
preparing a specimen by electrospraying a polymer sample, which is a mixed solution of a polymer compound, a matrix and a solvent, from a main nozzle onto a sample plate through a mask,
wherein a thickness deviation in the specimen is 30% or less, and
the mask comprises a hole through which the polymer sample is passed to the sample plate during the electrospraying.

2. The method for quantitative analysis of a polymer using MALDI mass spectrometry according to claim 1, wherein an error range of measurement results of a MALDI spectrum on the specimen (a relative standard deviation (RSD) of results of three experiments) is within 30%.

3. The method for quantitative analysis of a polymer using MALDI mass spectrometry according to claim 1, wherein an error range of measurement results of a MALDI spectrum on at least three specimens prepared under the same condition is within 30%.

4. The method for quantitative analysis of a polymer using MALDI mass spectrometry according to claim 1, wherein the polymer compound has a molecular weight of 1000 Da or more.

5. A method for preparing a specimen for MALDI mass spectrometry for quantitative analysis of a polymer, comprising:
providing an electrospray apparatus comprising a main nozzle for electrospray of a polymer sample which is a mixed solution of a polymer compound, a matrix and a solvent, and a sample plate on which the specimen is placed by electrospray of the polymer sample;
mounting a mask on the sample plate;
electrospraying of the polymer sample from the main nozzle onto the sample plate provided with the mask; and
obtaining the specimen of the polymer compound on the sample plate,
wherein the mask comprises a hole through which the polymer sample from the main nozzle is passed to the sample plate during the electrospraying so as to obtain a uniform specimen having a small thickness deviation on the sample plate.

6. The method for preparing a specimen for MALDI mass spectrometry for quantitative analysis of a polymer according to claim 5, wherein the hole has a diameter of 1 µm to 2 µm.

7. The method for preparing a specimen for MALDI mass spectrometry for quantitative analysis of a polymer according to claim 5, wherein the mask is made of stainless steel or aluminum.

8. The method for preparing a specimen for MALDI mass spectrometry for quantitative analysis of a polymer according to claim 5, wherein the mounting the mask on the sample plate further comprises adjusting a position of the mask in at least one of x-axis, y-axis, and z-axis directions.

9. The method for preparing a specimen for MALDI mass spectrometry for quantitative analysis of a polymer according to claim 5,
wherein the electrospray apparatus further comprises an auxiliary nozzle surrounding the main nozzle and coaxial with the main nozzle, and
the electrospraying the polymer sample from the main nozzle onto the sample plate further comprises spraying the solvent with the auxiliary nozzle to prevent the matrix from being deposited in a vicinity of the main nozzle.

10. The method for preparing a specimen for MALDI mass spectrometry for quantitative analysis of a polymer according to claim 9,
wherein the electrospray apparatus further comprises a sheath gas supply pipe surrounding the auxiliary nozzle and coaxial with the auxiliary nozzle, and
the electrospraying the polymer sample from the main nozzle onto the sample plate further comprises jetting a sheath gas through the sheath gas supply pipe so that the sheath gas guides the polymer sample to be sprayed onto a predetermined position of the sample plate.

11. A method for preparing a specimen for MALDI mass spectrometry for quantitative analysis of a polymer, comprising:
providing an electrospray apparatus comprising a main nozzle for electrospray of a polymer sample which is a mixed solution of a polymer compound, a matrix and a solvent, and a sample plate on which the specimen is placed by electrospray of the polymer sample;

electrospraying the polymer sample from the main nozzle onto the sample plate; and obtaining a specimen of the polymer sample on the sample plate, wherein the electrospraying the polymer sample from the main nozzle onto the sample plate further comprises at least one of:

(i) spraying the solvent from an auxiliary nozzle surrounding the main nozzle and coaxial with the main nozzle, so as to prevent the matrix from being deposited in a vicinity of the main nozzle, and (ii) jetting a sheath gas through a sheath gas supply pipe so that the sheath gas guides the polymer sample to be sprayed onto a predetermined position of the sample plate, so as to obtain a specimen having a thickness deviation of 30% or less.

12. The method for preparing a specimen for MALDI mass spectrometry for quantitative analysis of a polymer according to claim 5, wherein a jetting area through electrospray is 80 mm$^2$ or less.

* * * * *